United States Patent [19]

Cafruny et al.

[11] 4,029,776

[45] June 14, 1977

[54] THERAPEUTIC COMPOSITION AND METHOD OF USE THEREOF

[75] Inventors: Edward Joseph Cafruny, East Greenbush; Gordon Oliver Potts, Chatham, both of N.Y.

[73] Assignee: Sterling Drug Inc., New York, N.Y.

[22] Filed: Dec. 19, 1975

[21] Appl. No.: 642,677

[52] U.S. Cl. .................................................. 424/240
[51] Int. Cl.² ........................................... A61K 31/56
[58] Field of Search ..................................... 424/240

[56] References Cited

UNITED STATES PATENTS

| | | | |
|---|---|---|---|
| 3,257,390 | 6/1966 | Patchett | 424/240 |
| 3,296,255 | 1/1967 | Clinton et al. | 260/239.5 S |

Primary Examiner—Elbert L. Roberts
Attorney, Agent, or Firm—Thomas L. Johnson; B. Woodrow Wyatt

[57] ABSTRACT

A process for mitigating the secondary aldosteronism and potassium depletion induced by diuretic therapy involving oral administration, either simultaneously or sequentially with the diuretic, of $4\alpha,5$-epoxy-$17\beta$-hydroxy-3-oxo-$5\alpha$-androstane-$2\alpha$-carbonitrile; and a composition comprising a diuretic and said steroid compound.

8 Claims, No Drawings

THERAPEUTIC COMPOSITION AND METHOD OF USE THEREOF

BACKGROUND OF THE INVENTION

1. Field of the Invention

This invention relates to a process for reversing or preventing secondary aldosteronism and potassium depletion induced by diuretic therapy and to compositions useful for this purpose.

b 2. Description of the Prior Art

Most clincally useful oral diuretic agents not only cause loss of water from an animal organism, but also excretion of electroytes (natriuresis, kaluresis, etc.). The loss of sodium is frequently desirable in the treatment of edamatous conditions associated with heart failure and hypertension, but loss of potassium is undesirable as it causes muscular weakness and paralysis, and respiratory and cardiac disturbances. Examples of such diuretics are furosemide, ethacrynic acid and diuretics of the benzothiadiazine type, e.g. chlorothiazide, hydrochlorothiazide, flumethiazide, hydroflumethiazide, bendroflumethiazide, benzthiazide, cyclothiazide, methyclothiazide, polythiazide, trichlormethiazide; and related substances, e.g. chlorthalidone and quinethazone. Diuretics which are carbonic anhydrase inhibitors, e.g. acetozolamide, dichlorphenamide, ethoxyzolamide and methazolamide, also cause potassium loss.

Diuretic-caused hypokalemia has been treated by oral ingestion of potassium, e.g. potassium chloride, but this is often not well tolerated and if not carefully controlled can produce a hyperkalemic condition with its attendant risks such as cardiac arrest.

Spironolactone [3-(3-oxo-7α-acetylthio-17β-hydroxy-4-androsten-17α-yl)propionic acid lactone] is a diuretic acting by blocking the sodium-retaining, water-retaining and potassium excreting effect of aldosterone. Spironolactone is used in combination with hydrochlorothiazide as a diuretic which minimizes potassium loss. However, spironolactone has consistent undesirable, even unacceptable, side-effects on long-term administration.

4α,5-Epoxy-17β-hydroxy-3-oxo-5α-androstane-2α-carbonitrile having the formula

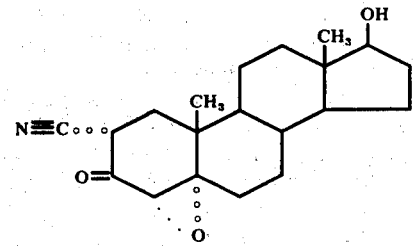

is disclosed in Clinton et al. U.S. Pat. 3,296,255, issued Jan. 3, 1967. It alters adrenal steriodogenesis and selectively blocks abnormal production of all adrenal cortical steriods, and is useful in the modulation and control of adrenocortical hyperfunction. This compound is not a diuretic per se.

SUMMARY OF THE INVENTION

In its process aspect, the invention relates to a process for reversing or preventing secondary aldosteronism and potassium depletion induced in a mammel undergoing diuretic therapy, which comprises administering orally to said mammal, sequentially or simultaneously, a substance having diuretic and electrolyte properties, and 4α,5-epoxy-17β-hydroxy-3-oxo-5α-androstane-2α-carbonitrile, the latter in amount effective to significantly reverse or prevent the secondary aldosteronism and potassium depletion caused by the diuretic alone.

In its composition of matter aspect, the invention relates to a diuretic composition comprising a substance having diuretic and electrolyte properties in combination with 4α,5-epoxy-17β-hydroxy-3-oxo-5α-androstane-2α-carbonitrile, the latter in proportional amount effective to significantly reverse or prevent the secondary aldosteronism and potassium depletion cause by the diuretic alone.

DETAILED DESCRIPTION INCLUSIVE OF PREFERRED EMBODIMENTS

Male rats of the Charles River strain with a mean body weight of 200 g. after an overnight fast were divided into four groups of 12 rats each. On the morning of test the animals were given Kreb's Ringer Phosphate solution, 5 ml/100 g intraperitoneally, and were placed in individual metabolism cages. Urines were then collected for 5 hours.

The vehicle (1% gum tragacanth) or furosemide was administered orally at 0, 2 and 4 hours. Urine collection started at 0 hours. The epoxy steriod or vehicle was administered orally in three doses given at 2 hour intervals starting two hours preceding the diuretic.

At the end of the 5 hour urine collection period, urine volumes were determined and urinary and plasma electrolytes determined by flame photometry.

The animals were anesthetized with sodium pentobarbital at the end of the urine collection to obtain plasma samples. Plasma volumes were determined utilizing an Evan's blue dye-dilution technique.

The twelve plasmas from each group were paired to yield six samples for steriod determinations. Aldosterone was determined after extraction and column chromatography.

The results obtained with the epoxy steroid in the absence of diuretic over a dose range of 6.25 to 25 mg/kg × 3 are presented in the following Table:

| Treatment | Oral Dose mg/kg t.i.d. | Urine Volume (5 hr) ml | Urine Electrolytes Total meq Na | K | Na/K |
|---|---|---|---|---|---|
| Vehicle | — | 4.8 ±1.0 | 0.70 ±0.14 | 0.21 ±0.03 | 3.5 ±0.5 |
| Epoxy Steroid | 6.25 | 3.9 ±0.3 | 0.59 ±0.04 | 0.19 ±0.02 | 2.7 ±0.3 |
| Epoxy Steroid | 12.5 | 6.0 ±0.8 | 0.74 ±0.09 | 0.16 ±0.02 | 5.3 ±0.7 |
| Epoxy Steroid | 25.0 | 5.7 ±0.8 | 0.66 ±0.12 | 0.11[a] ±0.01 | 6.3 ±0.9 |

| Treatment | Oral Dose mg/kg t.i.d. | Plasma Volume ml/100g | Na meq/l | K meq/l | Aldosterone ng/100 ml | Corticosterone μg/100 ml |
|---|---|---|---|---|---|---|
| Vehicle | — | 5.3 ±0.1 | 143 ±0.4 | 3.2 ±0.1 | 16.4 ±1.4 | 29.4 ±3.1 |
| Epoxy Steroid | 6.25 | 5.5 ±0.1 | 143 ±0.2 | 2.8 ±0.2 | 4.9[a] ±0.6 | 9.7[a] ±1.0 |
| Epoxy Steroid | 12.5 | 5.5 ±0.1 | 141 ±0.3 | 3.3 ±0.1 | 4.9[a] ±0.4 | 3.9[a] ±0.4 |
| Epoxy Steroid | 25.0 | 5.4 ±0.2 | 141 ±0.4 | 3.1 ±0.1 | 3.5[a] ±0.7 | 2.8[a] ±0.6 |

[a]Significantly different from vehicle values

The only change in the urinary excretion profile was a 50 percent reduction in urinary potassium produced by treatment with the high dose (25 mg/kg × 3) of the epoxy steriod.

The epoxy steroid, at all doses tested, reduced plasma aldosterone to minimally detectable levels. Corticosterone levels were reduced 70 percent by the low dose (6.25 mg/kg × 3) of the epoxy steroid and maximum reductions were obtained with the two higher dose levels. Plasma volume and plasma electrolytes were not altered by treatment with the epoxy steroid.

The next Table shows the effect of furosemide alone on urinary electrolytes and plasma corticoids in the rat:

| Treatment | Oral Dose mg/kg t.i.d. | Urine[a] Volume (5 hr) ml | Urine Electrolytes Total meq Na | K | Na/K |
|---|---|---|---|---|---|
| Vehicle | — | 4.9 ±0.4 | 0.39 ±0.05 | 0.16 ±0.01 | 2.4 ±0.2 |
| Furosemide | 12.5 | 12 ±1 | 1.24 ±0.06 | 0.39 ±0.02 | 3.3 ±0.2 |
| Furosemide | 25 | 17 ±0.3 | 1.80 ±0.04 | 0.48 ±0.01 | 3.8 ±0.1 |
| Furosemide | 50 | 20 ±0.4 | 2.34 ±0.04 | 0.53 ±0.02 | 4.5 ±0.1 |

| Treatment | Oral Dose mg/kg t.i.d. | Plasma[b] Volume ml/100g | Na meq/l | K meq/l | Aldosterone ng/100 ml | Corticosterone μg/100 ml |
|---|---|---|---|---|---|---|
| Vehicle | — | 4.4 ±0.1 | 141 ±0.3 | 3.0 ±0.1 | 25 ±3 | 33 ±2 |
| Furosemide | 12.5 | 3.8 ±0.04 | 140 ±0.3 | 3.0 ±0.1 | 43 ±4 | 46 ±3 |
| Furosemide | 25 | 3.7 ±0.1 | 140 ±0.3 | 2.9 ±0.1 | 18 ±3 | 52 ±2 |
| Furosemide | 50 | 3.4 ±0.1 | 140 ±0.3 | 3.1 ±0.1 | 60 ±3 | 56 ±3 |

[a]Furosemide values significantly different from vehicle alone
[b]Furosemide values, except for Na and K values, are significantly different from vehicle alone.

All doses of furosemide produced increases in urine volume and urinary electrolytes. Changes in urine volume and urinary sodium were dose related, however, maximum urinary potassium loss occurred with the dose of 25 mg/kg × 3. The Na/K ratio of the treated groups were increased significantly but only modestly over control, reflecting the increased excretion of both sodium and potassium. Plasma volumes were significantly reduced by all doses of furosemide, although plasma electrolytes were unaltered. Plasma levels of both aldosterone and corticosterone were elevated at all doses.

In the third Table below are listed the results of administration of both furosemide and the epoxy steroid. The furosemide was administered orally at 0, 2 and 4 hours. The epoxy steroid was administered orally in three doses given at 2 hour intervals starting 2 hours preceding the first does of diuretic.

| Treatment | Oral Dose mg/kg t.i.d. | Urine Volume (5 hr) ml | Urine Electrolytes Total meq Na | K | Na/K |
|---|---|---|---|---|---|
| Vehicle | — | 5.6 ±0.5 | 0.38 ±0.03 | 0.17 ±0.02 | 2.4 ±0.2 |
| Furosemide | 25 | 18[a] ±0.5 | 2.06[a] ±0.08 | 0.45[a] ±0.02 | 4.6[a] ±0.2 |
| Furosemide + Epoxy Steroid | 25 + 12.5 | 14[b] ±0.9 | 1.47[b] ±0.13 | 0.30[b] ±0.02 | 4.9 ±0.4 |
| Furosemide + Epoxy Steroid | 25 + 50 | 15 ±0.8 | 1.88 ±0.14 | 0.24[b] ±0.02 | 8.6[b] ±1.0 |

| Treatment | Oral Dose mg/kg t.i.d. | Plasma Volume ml/100g | Na meq/l | K meq/l | Aldosterone ng/100 ml | Corticosterone μg/100 ml |
|---|---|---|---|---|---|---|
| Vehicle | — | 4.8 ±0.1 | 144 ±0.4 | 3.2 ±0.1 | 5.2 ±0.4 | 19 ±5 |
| Furosemide | 25 | 4.0[a] ±0.1 | 142 ±0.5 | 2.9 ±0.1 | 21[a] ±3 | 53[a] ±3 |
| Furosemide + Epoxy Steroid | 25 + 12.5 | 4.2[a] ±0.1 | 141[a] ±0.5 | 2.9 ±0.1 | 5.7[b] ±1.3 | 14[b] ±2 |
| Furosemide + Epoxy Steroid | 25 + 50 | 3.9[a] ±0.1 | 141[a] ±0.5 | 3.0 ±0.1 | 3.8[b] ±0.6 | 5.1[b] ±0.9 |

[a]Values significantly different from controls (vehicle only)
[b]Values significantly different from furosemide alone.

In this test furosemide alone produced its characteristic response, i.e. increased urine volume and electrolyte excretion, a decreased plasma volume and increased plasma aldosterone and corticosterone levels.

The increases in plasma levels of both aldosterone and corticosterone produced by furosemide were completely prevented when either dose of the epoxy steroid was given in combination with the diuretic.

The administration of the epoxy steroid at either dose in combination with furosemide resulted in a reversal of the diuretic-induced kaluresis. In particular, the combination utilizing the higher dose of the epoxy steroid (50 mg/kg × 3) resulted in a urinary potassium excretion not significantly different from control (vehicle only); this occurred without altering the effects of furosemide or urine volume and sodium loss and thus produced almost a doubling in the urinary Na/K ratio. The reduction in plasma volume was comparable in the groups given furosemide and furosemide plus the epoxy steroid. The combination treatments however, did produce a modest but significant reduction in plasma sodium when compared with the vehicle-treated control.

In conclusion the administration of furosemide caused an increased urinary potassium excretion along with a loss in water and sodium. The potassium loss was of sufficient magnitude as to preclude a marked change in the urinary Na/K ratio. Furosemide increased plasma levels of both aldosterone and corticosterone in these studies. The epoxy steroid administered in combination with furosemide prevented the increased levels of corticosterone and aldosterone concomitant to increase in urinary potassium excretion. The beneficial effect of the potassium retention achieved by the epoxy steroid was accomplished without altering the effectiveness of furosemide in terms of sodium and water loss and consequently yielded a marked increase in the urinary Na/K ratio over that produced by diuretic alone.

Similar results have been obtained in which the furosemide was replaced by hydrochlorothiazide.

The administration of the epoxy steroid in conjunction with a diuretic is especially useful in the treatment of chronic hypertensive subjects undergoing diuretic therapy. The diuretic and epoxy steroid can be administered either sequentially in separate doses, or simultaneously as a combination dose of the two substances together with the administration repeated at selected time intervals dependent upon the severity of condition being treated.

In the event the diuretic and epoxy steroid are administered simultaneously, the two active substances can be administered as a mixture. Said mixture preferably contains the diuretic and epoxy steroid in a weight by weight ratio of between 2:1 and 1:2, respectively. The composition or mixture is conveniently prepared in unit dosage form as tablets or capsules together with conventional pharmaceutical excipients.

We claim:

1. A process for reversing or preventing secondary aldosteronism and potassium depletion induced in a mammal undergoing diuretic therapy, which comprises administering orally to said mammal, sequentially or simultaneously, a substance having diuretic and kaluretic properties, and 4α,5-epoxy-17β-hydroxy-3-oxo-5α-androstane-2α-carbonitrile, the latter in amount effective to significantly reverse or prevent the secondary aldosteronism and potassium depletion caused by the diuretic alone.

2. A process according to claim 1 in which the diuretic substance is furosemide.

3. A process according to claim 1 in which the diuretic substance is hydrochlorothiazide.

4. A diuretic composition comprising a substance having diuretic and kaluretic properties in combination with 4α,5-epoxy-17β-hydroxy-3-oxo-5α-androstane-2α-carbonitrile, the latter in proportional amount effective to significantly reverse or prevent the secondary aldosteronism and potassium depletion caused by the diuretic alone.

5. A composition according to claim 4 in which the diuretic composition is furosemide.

6. A composition according to claim 5 in which the furosemide and 4α,5-epoxy-17β-hydroxy-3-oxo-5α-androstane-2α-carbonitrile are present, respectively, in a weight by weight ratio of between 2:1 and 1:2.

7. A composition according to claim 4 in which the diuretic substance is hydrochlorothiazide.

8. A composition according to claim 7 in which the hydrochlorothiazide and 4α,5-epoxy-17β-hydroxy-3-oxo-5α-androstane-2αcarbonitrile are present, respectively, in a weight by weight ratio of between 2:1 and 1:2.

* * * * *

UNITED STATES PATENT AND TRADEMARK OFFICE
CERTIFICATE OF CORRECTION

PATENT NO. : 4,029,776
DATED : June 14, 1977
INVENTOR(S) : Edward Joseph Cafruny & Gordon Oliver Potts It is certified that error appears in the above-identified patent and that said Letters Patent are hereby corrected as shown below:

Column 1, line 14, "electroytes" should read --electrolytes--; line 16, "edamatous" should read --edematous--; line 27, "acetozolamide" should read --acetazolamide--; line 58, "steriodogenesis" should read --steroidogenesis--; line 67, "mammel" should read --mammal--.

Column 2, line 2 and line 10, after "electrolyte" insert --excretory-- (each instance); line 15, "cause" should read --caused--.

Column 3, line 33, "18" should read --48--; line 57, "does" should read --dose--.

Signed and Sealed this

First Day of November 1977

[SEAL]

Attest:

RUTH C. MASON
Attesting Officer

LUTRELLE F. PARKER
Acting Commissioner of Patents and Trademarks